United States Patent [19]
Castillo et al.

[11] Patent Number: 6,146,622
[45] Date of Patent: Nov. 14, 2000

[54] USE OF CERTAIN ANIONIC AMINO ACID BASED SURFACTANTS TO ENHANCE ANTIMICROBIAL EFFECTIVENESS OF TOPICALLY ADMINISTRABLE PHARMACEUTICAL COMPOSITIONS

[75] Inventors: Ernesto J. Castillo, Arlington; Steven Howard Gerson, Fort Worth; Wesley Wehsin Han, Arlington, all of Tex.

[73] Assignee: Alcon Laboratories, Inc., Forth Worth, Tex.

[21] Appl. No.: 09/399,698

[22] Filed: Sep. 21, 1999

Related U.S. Application Data

[60] Provisional application No. 60/105,854, Oct. 27, 1998.

[51] Int. Cl.$^7$ .......................... A61K 31/74; A61K 31/16; A61K 31/155
[52] U.S. Cl. ........................ 424/78.02; 424/78.04; 514/613; 514/634; 514/912
[58] Field of Search ............... 424/78.02, 78.04; 514/613, 634, 912

[56] References Cited

U.S. PATENT DOCUMENTS

| | | | |
|---|---|---|---|
| 3,275,503 | 9/1966 | Marnett et al. | 167/22 |
| 4,380,637 | 4/1983 | Lindemann et al. | 548/112 |
| 4,485,029 | 11/1984 | Kato et al. | 252/106 |
| 4,911,920 | 3/1990 | Jani et al. | 424/78 |
| 5,000,868 | 3/1991 | Wittpenn, Jr. et al. | 252/106 |
| 5,093,126 | 3/1992 | Jani et al. | 424/428 |
| 5,494,937 | 2/1996 | Asgharian et al. | 514/772.3 |
| 5,504,113 | 4/1996 | Lucero | 514/554 |
| 5,520,920 | 5/1996 | Castillo et al. | 424/402 |
| 5,536,305 | 7/1996 | Yu | 106/18.33 |
| 5,540,918 | 7/1996 | Castillo et al. | 424/78.04 |
| 5,631,218 | 5/1997 | Allan et al. | 510/423 |
| 5,641,480 | 6/1997 | Vermeer | 424/70.24 |
| 5,741,817 | 4/1998 | Chowhan et al. | 514/561 |

FOREIGN PATENT DOCUMENTS

| | | |
|---|---|---|
| 0 194 097 A1 | 9/1986 | European Pat. Off. . |
| 0 243 145 A2 | 10/1987 | European Pat. Off. . |
| 0 429 732 A1 | 6/1991 | European Pat. Off. . |

OTHER PUBLICATIONS

Cozzoli, *Preservative–Fee and Self–Preservig Cosmetics and Drugs: Principles and Practice*, Marcel Dekker, Inc., New York, NY, (1997), Chapter 4 "The Role of Surfactants in Self–Preserving Cosmetic Formulas".

Aminosoap AR–12 Product Brochure from Ajinomoto. U.S.A., Inc., Torrance, CA.

Aminosoap LYC–12S/LYC–12 Product Brochure from Ajinomoto .U.S.A., Inc., Torrance, CA.

Amisoft Anionic Surfactant Product Brochures from Ajinomoto .U.S.A., Inc., Torrance, CA.

Amilite GCK–12 Product Brochure from Ajinomoto .U.S.A., Inc., Torrance, CA.

Hamposyl Surfactants Product Brochure from Grace Organic Chemicals, Lexington, MA.

*Primary Examiner*—Kevin E. Weddington
*Attorney, Agent, or Firm*—Patrick M. Ryan

[57] ABSTRACT

Anionic amino acid based surfactants are used to enhance antimicrobial effectiveness in topically administrable pharmaceutical compositions containing at least one active ingredient, a cationic preservative and an anionic polyelectrolyte, such as carboxyvinyl polymers, xanthan gum, polystyrene sulfonic acid polymers and cationic exchange resins.

18 Claims, No Drawings

USE OF CERTAIN ANIONIC AMINO ACID BASED SURFACTANTS TO ENHANCE ANTIMICROBIAL EFFECTIVENESS OF TOPICALLY ADMINISTRABLE PHARMACEUTICAL COMPOSITIONS

This application claims priority to co-pending U.S. provisional application, Ser. No. 60/105,854, filed Oct. 27, 1998.

BACKGROUND OF THE INVENTION

The present invention relates generally to the preservation of pharmaceutical compositions. In particular, the present invention relates to the use of anionic surfactants, particularly amino acid based surfactants, to prevent or to reduce binding of the antimicrobial components of topically administrable pharmaceutical compositions to other components contained therein, thereby improving the antimicrobial efficacy of such compositions.

In recent years, a number of ophthalmic compositions have been introduced that contain a variety of components, such as carboxyvinyl polymers (e.g., Carbopol®), ion exchange resins (e.g., Amberlite®), or other large polyelectrolytes, which provide sustained release of the ophthalmic agent(s), as well as increased patient comfort. Such compositions are described, for example, in U.S. Pat. No. 4,911,920 (Jani et al.). Although these compositions are comfortable and have sustained release characteristics, cationic antimicrobials, such as benzalkonium chloride (BAC), which are often added as preservatives to such compositions, tend to bind to the anionic polyelectrolytes present in the formulations, resulting in loss of antimicrobial effectiveness.

Sarcosinate surfactants are composed of acylated sarcosines. Sarcosine ($CH_3$—NH—$CH_2$—COOH), an amino acid normally found in starfish and sea urchins, is chemically related to glycine ($NH_2$—$CH_2$—COOH), a basic amino acid in mammals. Common fatty acids and their derivatives utilized in the manufacture of sarcosinate surfactants are lauric, oleic, and myristic acids and their esters and halides. Because of their mildness, sarcosinate surfactants have been utilized in shampoos, mouthwashes, skin cleansers, sunscreens, aerosol shaving lathers and other personal care products. To date, the main applications of these types of surfactants have been in the cosmetic industry. For example, European Patent Application No. 0 194 097 (Schmidt et al.), assigned to Procter & Gamble, mentions sodium lauroyl sarcosinate as the mild anionic surfactant utilized in an aerosol skin-cleansing and moisturizer mousse.

U.S. Pat. No. 5,520,920 (Castillo, et al.) discloses the use of certain modified sarcosinates and lactylates to enhance antimicrobial effectiveness of ophthalmic compositions, particularly in the case where cationic preservatives otherwise bind to anionic polyelectrolytes. The modified sarcosinates have the formula:

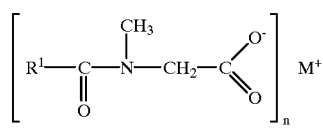

wherein: $R^1=C_4-C_{27}$ saturated or unsaturated hydrocarbon;
M=H or a pharmaceutically acceptable salt; and
n=1, 2 or 3.

Representative modified sarcosinates include those sold under the Hamposyl® trade name, such as lauroyl sarcosine (Hamposyl® L), oleoyl sarcosine (Hamposyl® O), myristoyl sarcosine (Hamposyl® M), cocoyl sarcosine (Hamposyl® C), stearoyl sarcosine (Hamposyl® S), and pelargodoyl sarcosine (Hamposyl® P). Representative lactylates include sodium capryl lactylate (Pationic® 122A).

Additional solutions to the problem of cationic preservative—anionic polyelectrolyte binding problem in topically administrable pharmaceutical compositions are desirable.

Anionic amino acid surfactants other than the Hamposyl® surfactants are known and include, for example, those surfactants sold under the Amilite™ and Amisoft™ trade names (Ajinomoto Co., Inc., Tokyo, Japan). According to its product brochure, one such surfactant, Amilite™ GCK-12, is used as a detergent, a foaming agent, an emulsifier, a solubilizer and a dispersing agent. Examples of applications of Amilite™ GCK-12 include cosmetics and toiletries (hair shampoo and body wash), face wash (facial washing foam, facial washing creme, facial washing liquid and make-up remover), facial soap, toothpaste, bath soap, contact lens cleaners and household cleaners. Amisoft™ surfactants are described as gentle cleansers for the skin and hair. Major applications of Amisoft™ surfactants include facial and body cleansers, hair shampoos, syndet bars, body care and dermatological products.

SUMMARY OF THE INVENTION

The present invention provides a method of enhancing the preservative efficacy of topically administrable pharmaceutical compositions containing an anionic polyelectrolyte and a cationic preservative. According to the method of the present invention, an anionic amino acid based surfactant is added to the topically administrable pharmaceutical composition. The anionic amino acid based surfactant has the formula:

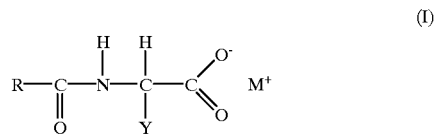

(I)

wherein: $R=C_8-C_{24}$ saturated or unsaturated hydrocarbon;
Y=H, $(CH_2)_4NH_2$ or $(CH_2)_3NHC(NH_2)=N^{+H}_2$; and
$M^{+=H}$ or a pharmaceutically acceptable salt.

Although the Applicants do not wish to be bound to a particular theory, it is believed that the addition of these anionic surfactants to the compositions results in the release of the bound cationic preservative from the anionic polyelectrolyte by the formation of a loose and reversible surfactant-preservative complex. The surfactant-preservative complex has antimicrobial effectiveness. Alternatively, the anionic surfactants of formula I may themselves possess antimicrobial activity.

Regardless of the mechanism, the anionic surfactants of the present invention improve the preservative efficacy of topically administrable pharmaceutical compositions. Accordingly, the present invention also relates to topically administrable pharmaceutical compositions containing one or more pharmaceutically active agents, an anionic polyelectrolyte, a cationic preservative, and one or more of the anionic amino acid based surfactants of formula I.

DETAILED DESCRIPTION OF THE INVENTION

Unless indicated otherwise, all amounts of composition ingredients expressed in percentage terms are expressed as weight/weight.

The anionic amino acid based surfactants of the present invention can be made by known methods and, in some cases, are commercially available. For example, Amilite™ GCK-12 is commercially available from Ajinomoto Co., Inc. (Tokyo, Japan). Amilite™ GCK-12 is described by formula I above when R is selected to be cocoyl, a coconut oil fatty acid residue; and M⁺ is K⁺ (i.e., potassium cocoyl glycinate).

Preferred surfactants of formula I include those where R is $C_{12}$–$C_{18}$ saturated or unsaturated hydrocarbon; Y is H; and M⁺ is selected from the group consisting of H⁺; Na⁺; K⁺; and triethanolamine.

In general, the amount of anionic amino acid based surfactant present in the compositions of the present invention is from about 0.001 to about 1%, preferably from about 0.01 to about 0.2%. For topical ophthalmic preparations, the concentration of the anionic amino acid based surfactant should be adjusted, usually in the 0.01 –0.1% range, to minimize patient discomfort.

The compositions of the present invention contain cationic antimicrobials and anionic polyelectrolytes. Cationic antimicrobials include quaternary ammonium compounds, such as benzalkonium chloride and polyquaternium-1. Anionic polyelectrolytes include high molecular weight, anionic mucomimetic polymers (e.g., carboxyvinyl polymers such as Carbopol®), polystyrene sulfonic acid polymers, cationic exchange resins (e.g., Amberlite® or Dowex®), and the like.

High molecular weight, anionic mucomimetic polymers have a molecular weight between about 50,000 and 6 million. The polymers are characterized as having carboxylic acid functional groups and preferably contain between 2 and 7 carbon atoms per functional group. Suitable high molecular weight, anionic polymers are carboxyvinyl polymers, preferably those called Carbomers, e.g., Carbopol® (B.F. Goodrich Co., Cleveland, Ohio). Specifically preferred are Carbopol® 934P, Carbopol® 974P and Carbopol® 940. Other suitable high molecular weight, anionic polymers include: alginates, carrageenans, natural gums (xanthan, karaya and tragacanth) and carboxy methyl cellulose. Such polymers will typically be employed in an amount between about 0.05 and about 6%, depending on the desired viscosity of the composition. Pourable liquid compositions generally comprise an amount of the polymer between about 0.05 and about 2%.

Cation exchange resins are characterized as either strongly acidic, such as those having sulfonic acid or sulfuric acid functionality, or weakly acidic, such as those having carboxylic acid functionality. Such resins are readily available, for example, from Rohm & Haas (Philadelphia, Pa.) under the name Amberlite® and from Dow Chemical Co. (Midland, Mich.) under the name Dowex®. The average particle size of the commercially available forms of the resins is about 40 to 150 microns. The particle size of the resin is critical for topically administrable ophthalmic compositions. Accordingly, for topically administrable ophthalmic compositions, commercially available resin particles are reduced by known techniques, including ball milling, to a particle size of about 20 µm or less such that the average particle size is ≦10 µm, and are preferably reduced to a particle size of about 10 µm or less. Ion exchange resins are typically used in an amount from about 0.05 to about 10%.

Anionic mucomimetic polymers and cation exchange resins are discussed in greater detail in U.S. Pat. No. 4,911,920 issued Mar. 27, 1990, the entire contents of which are hereby incorporated by reference herein.

The polystyrene sulfonic acid polymers (and their salts) useful in the compositions of the present invention comprise the following repeating unit:

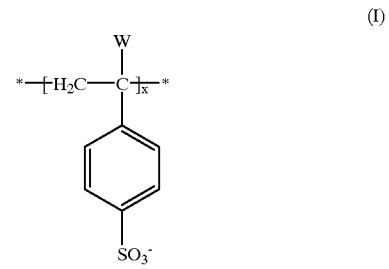

wherein: W=H or $CH_3$; and x=an integer such that the molecular weight of the polystyrene sulfonic acid polymer is from about 10,000 to 1.6 million.

In the preferred polystyrene sulfonic acid polymers of formula I, W=H and the molecular weight is between about 500,000 to about 1,000,000, preferably about 600,000. If present in the compositions of the present invention, the polystyrene sulfonic acid polymers of formula I comprise less than about 8%, preferably less than about 5%.

The active ingredient or ingredients that can be included in the compositions of the present invention include all ophthalmic, dermatological, otic or nasal agents that can be topically applied. For example, such ophthalmic agents include (but are not limited to): anti-glaucoma agents, such as beta-blockers (e.g., betaxolol and timolol), muscarinics (e.g., pilocarpine), prostaglandins, carbonic anhydrase inhibitors (e.g., acetazolamide, methazolamide and ethoxzolamide), dopaminergic agonists and antagonists, and alpha adrenergic receptor agonists, such as para-amino clonidine (also known as apraclonidine) and brimonidine; anti-infectives, such as ciprofloxacin; non-steroidal and steroidal anti-inflammatories, such as suprofen, ketorolac, dexamethasone, rimexolone and tetrahydrocortisol; proteins; growth factors, such as EGF; and anti-allergic agents, such as cromolyn sodium, emedastine and olopatadine. Compositions of the present invention may also include combinations of active ingredients. Most preferred are topically administrable ophthalmic compositions.

The compositions of the present invention can also include other components, for example, pharmaceutically acceptable buffers; tonicity agents; comfort-enhancing agents; solubilizing aids; pH adjusting agents; antioxidants; and stabilizing agents. The compositions may also contain additional preservatives (in conjunction with the cationic preservatives addressed above). As will be appreciated by those skilled in the art, the compositions may be formulated in various dosage forms suitable for topical delivery, including solutions, suspensions, emulsions, and gels.

The following examples are presented to illustrate further various aspects of the present invention, but are not intended to limit the scope of the invention in any respect.

EXAMPLE 1

| Ingredient | Concentration (%) |
|---|---|
| Betaxolol HCl | 0.28 |
| Amberlite IRP-69 | 0.25 |
| Carbopol 974P | 0.45 |
| Potassium Cocoyl Glycinate* | 0.03 |
| Boric Acid | 0.35 |
| Mannitol | 4.5 |
| Edetate Disodium | 0.01 |
| Benzalkonium Chloride | 0.01 + 10% xs |
| NaOH and/or HCl | q.s. to pH 6.5 |
| Purified Water | q.s. to 100 |

*Amilite GCK-12

Preparation:

0.42 g betaxolol hydrochloride and 0.375 grams of amberlite IRP 69 were stirred in ~25 mL of water for ~120 minutes. To this suspension were added 33.75 g of 2% carbopol 974P stock slurry, 0.525 g boric acid, 6.75 g mannitol, and 0.015 g disodium EDTA, 1.54 g of 1.07% BAC stock solution, and 0.15 g Amilite GCK-12 (30% potassium cocoyl glycinate.) The pH was adjusted to 6.5 by the addition of 5N sodium hydroxide and 1N hydrochloric acid and the formulation was brought to 150 g by the addition of water. The formulation is steam sterilized in an autoclave oven at 121° C., liquid cycle for 60 minutes.

EXAMPLE 2

| Ingredient | Concentration (%) |
|---|---|
| Levobetaxolol* HCl | 0.84 |
| Amberlite IRP-69 | 1.12 |
| Carbopol 974P | 0.35 |
| Potassium Cocoyl Glycinate** | 0.03 |
| Boric Acid | 0.5 |
| Mannitol | 3.3 |
| Edetate Disodium | 0.01 |
| Benzalkonium Chloride | 0.01 + 10% xs |
| Tromethamine | q.s. to pH 6.5 |
| Purified Water | q.s. to 100 |

*(S)-betaxolol
**Amilite GCK-12

EXAMPLE 3

| Ingredient | Concentration (%) |
|---|---|
| Betaxolol HCl | 0.28 |
| Amberlite IRP-69 | 0.25 |
| Carbopol 974P | 0.45 |
| Potassium Cocoyl Glycinate* | 0.06 |
| Boric Acid | 0.4 |
| Mannitol | 4.5 |
| Edetate Disodium | 0.01 |
| Benzalkonium Chloride | 0.01 |
| NaOH and/or HCl | q.s. to pH 7.2 |
| Purified Water | q.s. to 100 |

*Amilite GCK-12

EXAMPLE 4

| Ingredient | Concentration (%) |
|---|---|
| Betaxolol HCl | 0.28 |
| Amberlite IRP-69 | 0.25 |
| Carbopol 974P | 0.45 |
| Potassium Cocoyl Glycinate* | 0.03 |
| Boric Acid | 0.4 |
| Mannitol | 4.5 |
| Edetate Disodium | 0.01 |
| Benzalkonium Chloride | 0.01 + 10% xs |
| NaOH and/or HCl | q.s. to pH 6.5 |
| Purified Water | q.s. to 100 |

*Amilite GCK-12

EXAMPLE 5

Representative Formulation

| Ingredient | Concentration (%) |
|---|---|
| Betaxolol HCl | 0.28 |
| Brinzolamide | 1 |
| Amberlite IRP-69 | 0.25 |
| Carbopol 974P | 0.45 |
| Boric Acid | 0.4 |
| Mannitol | 4.5 |
| Potassium Cocoyl Glycinate* | 0.06 |
| Edetate Disodium | 0.01 |
| Benzalkonium Chloride | 0.01 |
| NaOH and/or HCl | q.s. to pH 6.5 |
| Purified Water | q.s. to 100 |

*Amilite GCK-12

COMPARATIVE EXAMPLE 1

| Ingredient | Concentration (%) |
|---|---|
| Betaxolol HCl | 0.28 |
| Amberlite IRP-69 | 0.25 |
| Carbopol 974P | 0.45 |
| Boric Acid | 0.4 |
| Mannitol | 4.5 |
| Edetate Disodium | 0.01 |
| Benzalkonium Chloride | 0.01 |
| NaOH and/or HCl | q.s. to pH 6.5 |
| Purified Water | q.s. to 100 |

COMPARATIVE EXAMPLE 2

| Ingredient | Concentration (%) |
|---|---|
| Betaxolol HCl | 0.28 |
| Benzalkonium Chloride | 0.01 |
| Carbopol 974P | 0.45 |
| Amberlite IRP-69 | 0.25 |
| Triethanolamine Cocoyl Glutamate* | 0.03 |
| Boric Acid | 0.4 |
| Mannitol | 4.5 |
| Edetate Disodium | 0.01 |
| NaOH and/or HCl | q.s. to pH 6.5 |
| Purified Water | q.s. to 100 |

*Amisoft CT-12

COMPARATIVE EXAMPLE 3

| Ingredient | Concentration (%) |
|---|---|
| Betaxolol HCl | 0.28 |
| Benzalkonium Chloride | 0.01 + 10% xs |
| Sodium Lauroyl Glutamate* | 0.03 |
| Carbopol 974P | 0.45 |
| Amberlite IRP-69 | 0.25 |
| Boric Acid | 0.4 |
| Mannitol | 4.15 |
| Edetate Disodium | 0.01 |
| Tromethamine | q.s. to pH 6.5 |
| Purified Water | q.s. to 100 |

*Amisoft LS-11

COMPARATIVE EXAMPLE 4

| Ingredient | Concentration (%) |
|---|---|
| Betaxolol HCl | 0.28 |
| Benzalkonium Chloride | 0.01 + 10% xs |
| Sodium Myristoyl Glutamate* | 0.03 |
| Carbopol 974P | 0.45 |
| Amberlite IRP-69 | 0.25 |
| Boric Acid | 0.4 |
| Mannitol | 4.15 |
| Edetate Disodium | 0.01 |
| Tromethamine | q.s. to 6.5 |
| Purified Water | q.s. to 100 |

*Amisoft MS-11

COMPARATIVE EXAMPLE 5

| Ingredient | Concentration (%) |
|---|---|
| Betaxolol HCl | 0.28 |
| Benzalkonium Chloride | 0.01 + 10% xs |
| Sodium Stearoyl Glutamate* | 0.03 |
| Carbopol 974P | 0.45 |
| Amberlite IRP-69 | 0.25 |
| Boric Acid | 0.4 |
| Mannitol | 4.15 |
| Edetate Disodium | 0.01 |
| Tromethamine | q.s. to pH 6.5 |
| Purified Water | q.s. to 100 |

*Amisoft HS-11

COMPARATIVE EXAMPLE 6

| Ingredient | Concentration (%) |
|---|---|
| Betaxolol HCl | 0.28 |
| Benzalkonium Chloride | 0.01 + 10% xs |
| Carbopol 974P | 0.45 |
| Triethanolamine Cocoyl Glutamate* | 0.03 |
| Amberlite IRP-69 | 0.25 |
| Boric Acid | 0.4 |
| Mannitol | 4.5 |
| Edetate Disodium | 0.01 |
| Tromethamine | q.s. to pH 6.5 |
| Purified Water | q.s. to 100 |

*Amisoft CT-12

COMPARATIVE EXAMPLE 7

| Ingredient | Concentration (%) |
|---|---|
| Benzalkonium Chloride | 0.01 |
| Mannitol | 5 |
| Purified Water | q.s. to 100 |

COMPARATIVE EXAMPLE 8

| Ingredient | Concentration (%) |
|---|---|
| Benzalkonium Chloride | 0.01 |
| Boric Acid | 0.4 |
| Mannitol | 4.9 |
| Tromethamine | 0.726 |
| Edetate Disodium | 0.01 |
| Purified Water | q.s. to 100 |

EXAMPLE 6

Antimicrobial preservative effectiveness was determined using an organism challenge test according to the methods described in the United States Pharmacopeia (USP) and European Pharmacopoeia (Ph.Eur.). Samples were inoculated with known levels of one or more of the following: gram-positive (*Staphylococcus aureus* ATCC 6538) and gram-negative (*Pseudomonas aeruginosa* ATCC 9027 and *Escherichia coli* ATCC 8739) vegetative bacteria, yeast (*Candida albicans* ATCC 10231) and mold (*Aspergillus niger* ATCC 16404). The samples were then pulled at specified intervals to determine if the antimicrobial preservative system was capable of killing or inhibiting the propagation of organisms purposely introduced into the formulation. The rate or level of antimicrobial activity determined compliance with the USP and/or Ph.Eur. preservative efficacy standards for ophthalmic preparations.

The compendial preservative standards for ophthalmic preparations are presented below:

| | Log Reduction of Organism Population | | |
|---|---|---|---|
| Time Pull | USP | Ph.Eur. A (Target) | Ph.Eur. B (Min) |
| For Bacteria: | | | |
| 6 hours | — | 2 | — |
| 24 hours | — | 3 | 1 |
| 7 days | — | — | 3 |
| 14 days | 3 | — | — |
| 28 days | NI | NR | NI |
| For Fungi: | | | |
| 7 days | — | 2 | — |
| 14 days | NI | — | 1 |
| 28 days | NI | NI | NI |

NR = No organisms recovered
NI = No increase at this or any following time pulls
— = No requirement at this time pull The results of the microorganism challenge tests are shown in Tables 1 and 2 below.

TABLE 1

| | Preservative Efficacy Standard | | |
|---|---|---|---|
| Formulation | USP | Ph.Eur. B (Minimum) | Ph.Eur. A |
| Example 4 | Pass | Pass | Fail |
| Comp. Ex. 1 | Pass | Fail | Fail |

TABLE 2

| | Organism (7 day results-log reduction) | | | | |
|---|---|---|---|---|---|
| Formulation | S. aureus | P. aeruginosa | E. coli | C. albicans | A. niger |
| Example 1 | 4.9 | 4.9 | — | — | 0.5 |
| Example 2 | 5.1 | 4.9 | — | — | 1.8 |
| Example 3 | 5.2 | 5.0 | — | — | 0.3 |
| Comp. Ex. 2 | 2.9 | 5.0 | — | — | 1.3 |
| Comp. Ex. 3 | 0.0 | 5.0 | — | — | 2.9 |
| Comp. Ex. 4 | 1.5 | 5.0 | — | — | 3.5 |
| Comp. Ex. 5 | 2.1 | 5.0 | — | — | 3.6 |
| Comp. Ex. 6 | 0.5 | 5.0 | 5.0 | 1.6 | 2.0 |
| Comp. Ex. 7 | 4.8 | 4.7 | 4.9 | 4.7 | 2.5 |
| Comp. Ex. 8 | 4.8 | 4.7 | 4.9 | 4.7 | 3.7 |

The invention in its broader aspects is not limited to the specific details shown and described above. Departures may be made from such details within the scope of the accompanying claims without departing from the principles of the invention and without sacrificing its advantages.

We claim:

1. A method of improving or enhancing the antimicrobial efficacy of a topically administrable pharmaceutical composition comprising a cationic antimicrobial, an anionic polyelectrolyte and an active ingredient, wherein the method comprises adding to the composition an antimicrobial-enhancing amount of an anionic amino acid based surfactant of the formula:

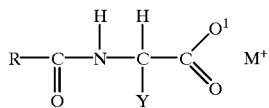

wherein: $R = C_8 - C_{24}$ saturated or unsaturated hydrocarbon;

Y=H, $(CH_2)_4 NH_2$ or $(CH_2)_3 NHC(NH_2)=N^+H_2$; and $M^+$=H or a pharmaceutically acceptable salt.

2. The method of claim 1 wherein R is $C_{12}-C_{18}$ saturated or unsaturated hydrocarbon; Y is H; and $M^+$ is selected from the group consisting of $H^+$; $Na^+$; $K^+$; and triethanolamine.

3. The method of claim 2 wherein the anionic amino acid based surfactant is potassium cocoyl glycinate.

4. The method of claim 1 wherein the antimicrobial-enhancing amount of fatty acid/amino acid soap is from about 0.001 to about 1%.

5. The method of claim 4 wherein the antimicrobial-enhancing amount of fatty acid/amino acid soap is from about 0.01 to about 0.2%.

6. The method of claim 1 wherein the anionic polyelectrolyte is selected from the group consisting of: carboxyvinyl polymers; xanthan gum, polystyrene sulfonic acid polymers; and cationic exchange resins.

7. The method of claim 1 wherein the topically administrable pharmaceutical composition further comprises one or more active ingredients selected from the group consisting of ophthalmic; dermatological; otic; and nasal agents.

8. The method of claim 7 wherein the topically administrable pharmaceutical composition comprises an ophthalmic agent selected from the group consisting of anti-glaucoma agents; anti-infectives; non-steroidal and steroidal anti-inflammatories; proteins; growth factors; and anti-allergic agents.

9. The method of claim 7 wherein the topically administrable pharmaceutical composition further comprises one or more ingredients selected from the group consisting of pharmaceutically acceptable buffers; tonicity agents; comfort-enhancing agents; solubilizing aids; pH adjusting agents; antioxidants; and stabilizing agents.

10. A topically administrable pharmaceutical composition comprising a cationic antimicrobial, an anionic polyelectrolyte, an active ingredient, and an antimicrobial-enhancing amount of an anionic amino acid based surfactant of the formula:

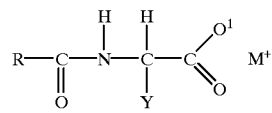

wherein: $R = C_8 - C_{24}$ saturated or unsaturated hydrocarbon;

Y=H, $(CH_2)_4 NH_2$ or $(CH_2)_3 NHC(NH_2)=N^+H_2$; and $M^+$=H or a pharmaceutically acceptable salt.

11. The composition of claim 10 wherein R is $C_{12}-C_{18}$ saturated or unsaturated hydrocarbon; Y is H; and $M^+$ is selected from the group consisting of $H^+$; $Na^+$; $K^+$; and triethanolamine.

12. The composition of claim 11 wherein the anionic amino acid based surfactant is potassium cocoyl glycinate.

13. The composition of claim 10 wherein the antimicrobial-enhancing amount of the anionic amino acid based surfactant is from about 0.001 to about 1%.

14. The composition of claim 13 wherein the antimicrobial-enhancing amount of the anionic amino acid based surfactant is from about 0.01 to about 0.2%.

15. The composition of claim 10 wherein the anionic polyelectrolyte is selected from the group consisting of: carboxyvinyl polymers; xanthan gum; polystyrene sulfonic acid polymers; and cationic exchange resins.

16. The composition of claim 10 wherein the topically administrable pharmaceutical composition further comprises one or more active ingredients selected from the group consisting of ophthalmic; dermatological; otic; and nasal agents.

17. The composition of claim 16 wherein the topically administrable pharmaceutical composition comprises an ophthalmic agent selected from the group consisting of anti-glaucoma agents; anti-infectives; non-steroidal and steroidal anti-inflammatories; proteins; growth factors; and anti-allergic agents.

18. The composition of claim 16 wherein the topically administrable pharmaceutical composition further comprises one or more ingredients selected from the group consisting of pharmaceutically acceptable buffers; tonicity agents; comfort-enhancing agents; solubilizing aids; pH adjusting agents; antioxidants; and stabilizing agents.

* * * * *